US008657804B2

(12) United States Patent
Horne et al.

(10) Patent No.: US 8,657,804 B2
(45) Date of Patent: Feb. 25, 2014

(54) VISUAL INDICATION OF RUPTURE OF DRUG RESERVOIR

(75) Inventors: Kenneth N. Horne, San Francisco, CA (US); Gregory J. R. Spooner, San Francisco, CA (US); John A. Scholl, San Ramon, CA (US); John T. Santini, Jr., North Chelmsford, MA (US)

(73) Assignee: On Demand Therapeutics, Inc., Tyngsboro, MA (US)

( * ) Notice: Subject to any disclaimer, the term of this patent is extended or adjusted under 35 U.S.C. 154(b) by 544 days.

(21) Appl. No.: 12/910,572

(22) Filed: Oct. 22, 2010

(65) Prior Publication Data

US 2011/0098640 A1    Apr. 28, 2011

Related U.S. Application Data

(60) Provisional application No. 61/254,179, filed on Oct. 22, 2009.

(51) Int. Cl.
*A61M 31/00* (2006.01)
(52) U.S. Cl.
USPC ........................................................ 604/521
(58) Field of Classification Search
USPC .......... 600/473–480, 407; 604/264, 290, 521, 604/890.1–892.1
See application file for complete search history.

(56) References Cited

U.S. PATENT DOCUMENTS

| 6,976,982 | B2 | 12/2005 | Santini, Jr. et al. | |
| 7,776,024 | B2 | 8/2010 | Santini, Jr. et al. | |
| 2002/0099359 | A1* | 7/2002 | Santini et al. | 604/521 |
| 2006/0204534 | A1 | 9/2006 | Blinn et al. | |
| 2008/0138289 | A1* | 6/2008 | Goronkin et al. | 424/9.4 |
| 2009/0196903 | A1* | 8/2009 | Kliman | 424/423 |

FOREIGN PATENT DOCUMENTS

| WO | 2009/097468 A2 | 8/2009 |
| WO | 2009/097468 A3 | 10/2009 |

OTHER PUBLICATIONS

International Search Report and Written Opinion received for PCT Patent Application No. PCT/US2010/053705, mailed on Feb. 3, 2011, 15 pages.
Santini, J. et al. (Jan. 28, 1999). "A controlled-release microchip," *Nature* 397:335-338.

* cited by examiner

*Primary Examiner* — Matthew F Desanto
(74) *Attorney, Agent, or Firm* — Sutherland Asbill & Brennan LLP

(57) ABSTRACT

The present disclosure relates to methods for visualizing the opening of a drug reservoir of an implantable medical device. In particular, the present disclosure provides methods for observing the release or exposure of contents from a drug reservoir of a medical device placed within the vitreous of an eye of a subject. The methods include implanting a drug delivery device within an anatomy of a subject. The drug device includes a plurality of reservoirs, each loaded with a therapeutic agent and a marker. Furthermore, the drug delivery device comprises a plurality of barrier layers for separating the contents of one of the plurality of reservoirs from the anatomy. The method further includes irradiating at least one of the plurality of barrier layers such that at least one of the plurality of reservoirs is breached, thereby triggering release of the therapeutic agent and the marker from the device. By visually detecting release of the marker into the anatomy, release of the therapeutic agent into the anatomy is verified.

22 Claims, 6 Drawing Sheets
(2 of 6 Drawing Sheet(s) Filed in Color)

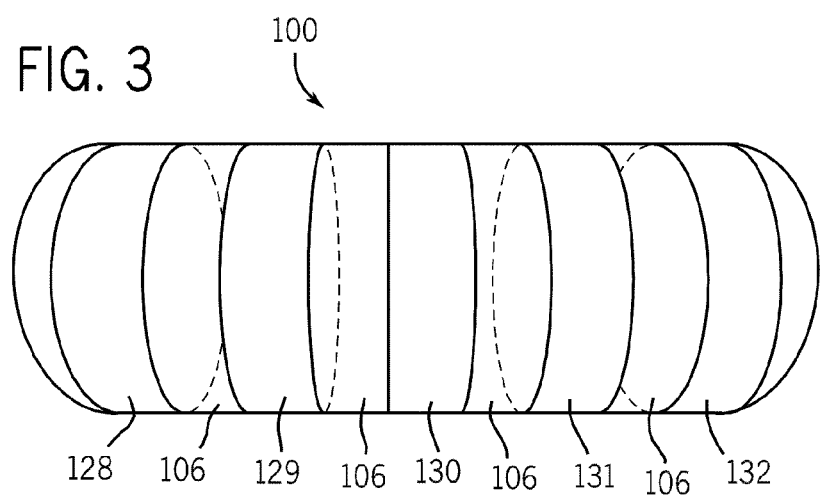
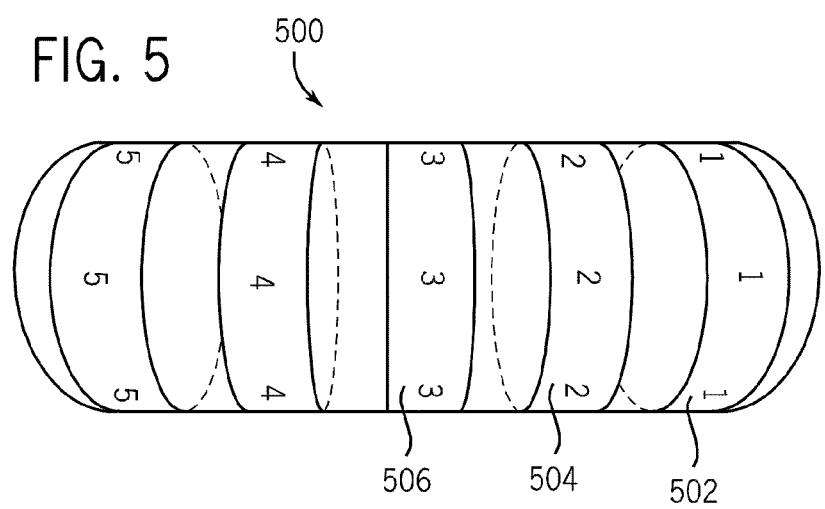

Zeiss FF450 fundus photo
Group C eye ~ 1 hour post laser

VISUAL INDICATION OF RUPTURE OF DRUG RESERVOIR

CROSS-REFERENCE TO RELATED APPLICATIONS

This application claims the priority benefit of U.S. provisional application Ser. No. 61/254,179, filed Oct. 22, 2009, which is incorporated herein by reference in its entirety.

FIELD

The present disclosure provides methods for a physician to determine which of the drug delivery device's drug reservoirs contain drug and which ones have already been opened to release their drug contents. Additionally, the present disclosure provides methods for a physician to identify the individual drug reservoirs of an implantable drug delivery device while the drug delivery device resides in the body of a subject. The present disclosure also relates to methods for visualizing the opening of a drug reservoir of an implantable medical drug delivery device. In particular, the present disclosure provides methods for observing a visual indication of the release of contents from a drug reservoir of a drug delivery device placed within the vitreous of an eye of a subject. Alternatively, the present disclosure provides methods for observing a visual indication of the exposure of the contents of a drug reservoir of a medical drug delivery device placed within the vitreous of an eye of a subject.

BACKGROUND

Implantable drug delivery devices are used to deliver various types of therapeutic agents. For example, drug-eluting stents release an anti-proliferative agent such as sirolimus or paclitaxel into the wall of the blood vessel in contact with the stent to prevent fibrosis by implantable polymer reservoirs slowly eluting drug at a pre-determined rate into the surrounding tissue. Previously, it has been difficult to determine whether the therapeutic agent is being or has been correctly released because there may be no way to directly or indirectly visualize changes in the drug delivery device or the mechanism of drug release while the drug delivery device is inside the subject. Release can be confirmed analytically by assaying a blood or tissue sample taken from a patient for the presence of the therapeutic agent or by looking for the expected clinical improvement in the patient's condition. However, these methods may present therapeutic, diagnostic, economic, or simply logistical drawbacks since confirmation of drug release from the implantable drug delivery device is not immediate and may be based on indirect or secondary indicators of release such as biomarkers or physiologic changes in the subject. Accordingly there is a need in the art for methods of assessing, during a visit to a health care provider, whether a therapeutic agent is being or has been properly delivered by an implantable drug delivery device. In particular, the ability to non-invasively visualize the inside of the eye provides an opportunity to develop methods for observing the condition of an implantable drug delivery device and confirming drug release while the drug delivery device resides in the subject's eye.

Examples of drug delivery devices for ophthalmic applications are described in the following, which are all incorporated herein by reference: U.S. Pat. No. 6,976,982, U.S. Pat. No. 7,582,080, US 2008/0221557, U.S. Pat. No. 7,776,024, AU 200241834, CN 2432438, EU 1372602, JP 4354521, JP 2002-555792, JP 2009-277085.

SUMMARY

The present disclosure provides methods for a physician to identify the individual drug reservoirs of an implantable drug delivery device while the drug delivery device resides in the body of a subject. Additionally, the present disclosure provides methods for a physician to determine which of the drug delivery device's drug reservoirs contain drug and which ones have already been opened to release their drug contents. The present disclosure also relates to methods for visualizing the opening of a drug reservoir of an implantable drug delivery device. In particular, the present disclosure provides methods for observing the release of contents from a drug reservoir of a drug delivery device placed within the vitreous of an eye of a subject. Alternatively, the present disclosure provides methods for observing the exposure of the contents of a drug reservoir of a drug delivery device placed within the vitreous of an eye of a subject.

Specifically, the present disclosure provides methods comprising: a) implanting a drug delivery device within the anatomy of a subject, wherein the drug delivery device comprises: i) a plurality of reservoirs, each loaded with a therapeutic agent and a marker; and ii) a plurality of barrier layers, each separating the contents of one of the plurality of reservoirs from the anatomy; b) irradiating at least one of the plurality of barrier layers such that at least one of the plurality of reservoirs is breached, thereby triggering release of the therapeutic agent and the marker from the drug delivery device; and c) visually detecting release of the marker into the anatomy in order to verify release of the therapeutic agent into the anatomy. In some preferred embodiments, the marker is a fluorophore and the visually detecting is accomplished by use of a fluorophotometer, and in a subset of these embodiments, the fluorophore may be fluorescein, rose Bengal, indocyanine green, rhodamine, or any derivative thereof, for example.

In some embodiments, the therapeutic agent comprises one or more of anti-inflammatories, anti-infectives, anti-allergens, cholinergic agonists and antagonists, adrenergic agonists and antagonists, anti-glaucoma agents, agents for cataract prevention or treatment, neuroprotective agents, antioxidants, antihistamines, anti-platelet agents, anticoagulants, anti-thrombic agents, anti-scarring agents, anti-proliferatives, anti-tumor agents, complement factors, complement inhibitors, decongestants, vitamins, growth factors, anti-growth factor agents, gene therapy vectors, chemotherapy agents, protein kinase inhibitors, small interfering RNAs, limus family compounds, antibody fragments, and combinations thereof. In some preferred embodiments, the anti-growth factor agent is at least one of an anti-vascular endothelial growth factor (anti-VEGF) agent, anti-platelet-derived growth factor (anti-PDGF) agent, and anti-placental growth factor (anti-PLGF) agent, for example. In some particularly preferred embodiments the anti-VEGF agent is one or more of the following, for example: aflibercept (VEGF trap), bevacizumab (AVASTIN), pegaptanib sodium (MACUGEN), and ranibizumab (LUCENTIS). In some embodiments, the complement factor is complement factor H, for example. In some embodiments, the complement inhibitor is a S1P inhibitor, mTOR inhibitor, factor B, factor C3, factor D, or C5 aptamer, for example. A complement inhibitor may be Eclizumab, for example. A S1P inhibitor may be, for example, Sonepcizumab. An mTOR inhibitor may be, for example, Sirolimus or Everolimus. In other embodiments, the anti-inflammatory is a steroidal agent. In some preferred embodiments, the steroidal agent is selected from the group including dexamethasone, triamcinolone, and fluocinolone, for example. An example of fluocinolone is Illuvien. An example of an antibody fragment is ESBA105. Furthermore, in other embodiments, the therapeutic agent may be a sphingomab, such as iSONEP, an anti-PDGF pegylated aptamer, an a5b1 integrin antagonist, or a NADPH Oxidase Inhibitor, for example.

The present disclosure provides embodiments in which the marker is covalently linked to the therapeutic agent, as well as embodiments in which the marker is not linked to the therapeutic agent. In some embodiments, the marker is configured as a coating encapsulating the therapeutic agent so that at least a portion of the marker is released before any drug is released from the reservoir. In some embodiments, the marker is mixed or co-formulated with the therapeutic agent so that the marker and therapeutic agent are released simultaneously. In other embodiments, the marker is contained in the therapeutic agent as a small pellet or aggregation of marker that is only exposed and released once most or all of the drug released. In some preferred embodiments, the irradiating comprises application of optical radiation from a laser. The laser may be an argon ion laser, a Nd:YAG laser, a frequency-doubled Nd:YAG laser, a diode laser, a Nd:YLF laser, a krypton laser, a dye laser, or a helium-neon laser, for example. In some embodiments, the implanting comprises placement of the drug delivery device within or adjacent to an ocular region of the subject. In some preferred embodiments, the ocular region may be a sclera, a cornea, a choroid, a pars plana, a retina, a vitreous body, or a conjunctiva, for example. In some preferred embodiments, the implanting comprises intravitreal injection or insertion of the drug delivery device. Also provided by the present disclosure are methods suitable for treating or preventing a condition, such as wet or dry age-related macular degeneration (AMD), choroidal neovascularization (CNV), diabetic retinopathy, branch retinal vein occlusion (BRVO), central retinal vein occlusion (CRVO), macular edema, diabetic macular edema (DME), cancer, glaucoma, retinal and choroidal disease, cataracts, dry eye syndrome, optic neuropathy, orbital disease, corneal conditions, retinitis pigmentosa, uveitis, and other diseases or conditions of the eye. In some embodiments, the methods further comprise: d) distinguishing between an unloaded or empty reservoir and at least one loaded reservoir, wherein the unloaded reservoir is produced due to essentially complete release of the therapeutic agent and the marker, and wherein the at least one loaded reservoir still contains the therapeutic agent and the marker; e) irradiating at least one of the plurality of barrier layers such that the at least one loaded reservoir is breached, thereby triggering further release of the therapeutic agent and the marker from the drug delivery device; and f) visually detecting release of the marker from the loaded reservoir into the anatomy in order to verify further release of the therapeutic agent. In some preferred embodiments, the methods further comprise repeating steps d-f until all of the plurality of reservoirs are unloaded reservoirs.

Moreover the present disclosure provides methods comprising: a) implanting a drug delivery device within anatomy of a subject, wherein the drug delivery device comprises: i) a plurality of reservoirs, each loaded with a therapeutic agent; and ii) a plurality of barrier layers, each separating contents of one of the plurality of reservoirs from the anatomy; b) irradiating at least one of the plurality of barrier layers such that at least one of the plurality of reservoirs becomes a breached reservoir that generates or exposes a visual indicator, and c) visually detecting the visual indicator in order to verify exposure of the therapeutic agent to the anatomy.

In some embodiments, the visual indicator comprises an air bubble and the visually detecting is accomplished by use of an ophthalmic slit-lamp microscope. In other embodiments, the visual indicator comprises a hole in the barrier layer that can be visually detected by use of an ophthalmic slit-lamp microscope.

In some embodiments, the therapeutic agent comprises one or more of: anti-inflammatories, an anti-infectives, an anti-allergens, cholinergic agonists and antagonists, adrenergic agonists and antagonists, anti-glaucoma agents, agents for cataract prevention or treatment, neuroprotection agents, anti-oxidants, antihistamines, anti-platelet agents, anti-coagulants, anti-thrombic agents, anti-scarring agents, anti-proliferatives, anti-tumor agents, complement inhibitors, decongestants, vitamins, growth factors, anti-growth factor agents, gene therapy vectors, chemotherapy agents, protein kinase inhibitors, small interfering RNAs, limus family compounds, or combinations thereof, for example.

In some preferred embodiments, the anti-growth factor agent is an anti-vascular endothelial growth factor (anti-VEGF) agent. In some particularly preferred embodiments the anti-VEGF agent is one or more of the following: aflibercept (VEGF trap), bevacizumab (AVASTIN), pegaptanib sodium (MACUGEN), ranibizumab (LUCENTIS), or combinations thereof, for example.

In other embodiments, the anti-inflammatory is a steroidal agent. In some preferred embodiments, the steroidal agent is dexamethasone, triamcinolone, or fluocinolone, for example.

In some preferred embodiments, the irradiating comprises application of a laser, such as an argon ion laser, a Nd:YAG laser, a frequency-doubled Nd:YAG laser, a diode laser, a Nd:YLF laser, a krypton laser, a dye laser, or a helium-neon laser.

In some embodiments, the implanting comprises placement of the drug delivery device within or adjacent to an ocular region of the subject.

In some preferred embodiments, the ocular region may be a sclera, a cornea, a choroid, a retina, a vitreous body, or a conjunctiva, for example. In some preferred embodiments, the implanting comprises intravitreal injection of the device. Also provided by the present disclosure are methods suitable for treating or preventing conditions, such as age-related macular degeneration, diabetic retinopathy, branch retinal vein occlusion, central retinal vein occlusion, macular edema, cancer, glaucoma, retinal and choroidal disease, cataracts, dry eye syndrome, optic neuropathy, orbital disease, corneal conditions, uveitis, and any condition listed in Table B above. In some embodiments, the methods further comprise: d) distinguishing between an unloaded or empty reservoir and at least one loaded reservoir, wherein the unloaded reservoir is produced due to essentially complete release of the therapeutic agent, and wherein the at least one loaded reservoir still contains the therapeutic agent; e) irradiating at least one of the plurality of barrier layers such that the at least one loaded reservoir becomes a breached reservoir that generates or exposes the visual indicator; and f) visually detecting the visual indicator in order to verify further exposure of the therapeutic agent to the anatomy. In some preferred embodiments, the methods further comprise repeating steps d-f until all of the plurality of reservoirs are unloaded reservoirs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates the embodiment of the drug delivery device.

FIG. 4A depicts a laser beam perforating a barrier layer of a drug reservoir to liberate a therapeutic agent and a marker contained therein, leaving an empty reservoir as shown in FIGS. 4B and 4C, respectively. FIG. 4D depicts a laser beam perforating barrier layers of a marker envelope and a drug reservoir to liberate a marker and a therapeutic agent, leaving an empty envelope and reservoir as shown in FIGS. 4E and 4F, respectively.

FIG. 5 illustrates another embodiment of the drug delivery device.

DETAILED DESCRIPTION

Figure 1:
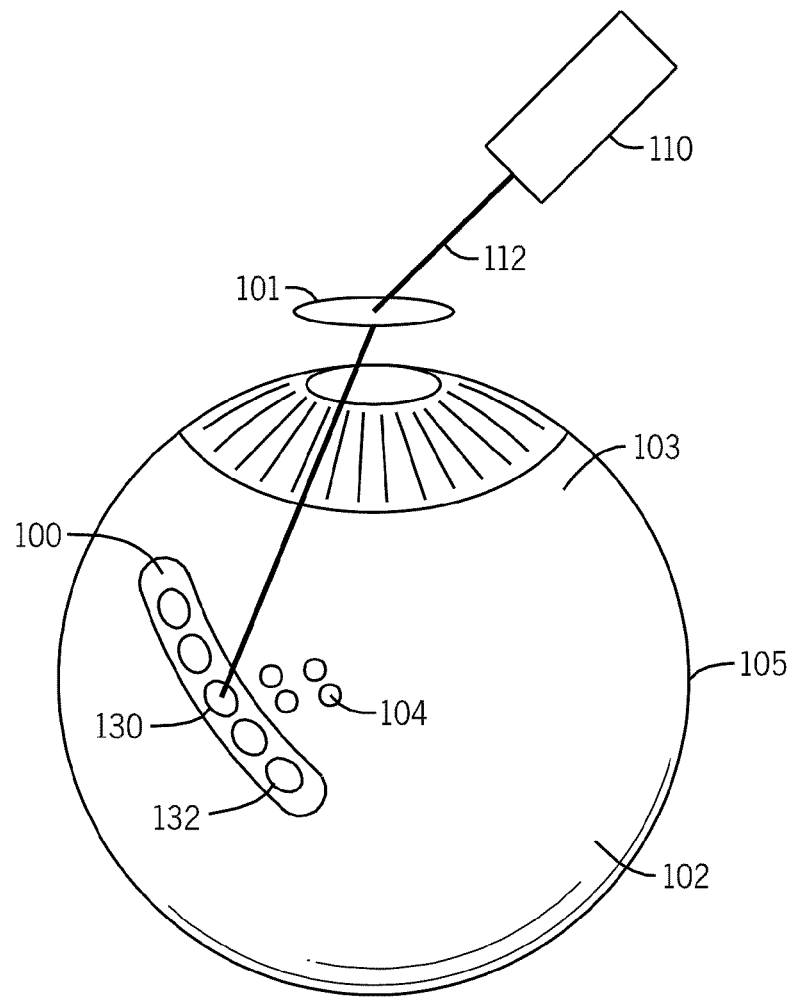
FIG. 1 illustrates one embodiment of a drug delivery device that has been implanted into the vitreous body of an eye.

The present disclosure provides methods for a physician to identify the individual drug reservoirs of an implantable drug delivery device while the drug delivery device resides in the body of a subject. Additionally, the present disclosure provides methods for a physician to determine which of the drug delivery device's drug reservoirs contain drug and which ones have already been opened to release their drug contents. The present disclosure relates to methods for visualizing the opening of a drug reservoir of an implantable medical drug delivery device. In particular, the present disclosure provides methods for directly or indirectly observing the release or exposure of contents from a drug reservoir of a medical drug delivery device placed within the vitreous of an eye of a subject.

In some cases, such as when the implanted drug delivery device is visibly observable (e.g., placed in the shallow dermis or epidermis, in endoscopically-accessible areas, or most relevantly, in the transparent structures of the eye), the opening of a drug reservoir of the drug delivery device can be directly observed. This is particularly advantageous when a treatment regimen requires periodic and local administration of a therapeutic agent.

In conventional ocular posterior chamber drug therapy, a therapeutic agent is directly injected into one or both eyes of a patient. The physician receives definite visual feedback that the drug payload has been delivered by virtue of the injection needle being inserted to a particular depth in the anatomy, and the syringe being emptied of its contents in a visually obvious way (i.e. the depressing of the syringe's plunger). As described in this disclosure, the release of a visible indicator (e.g., a marker) during laser activation of a drug reservoir of an exemplary implantable drug delivery device is a valuable tool for confirming that laser activation was successful in creating an opening in the drug reservoir. An indication from the implantable drug delivery device that the barrier of a drug reservoir has been altered, activated, perforated, breached, etc., and that the therapeutic agent contained therein will subsequently begin eluting, provides the same level of confidence as conventional intraocular injection that a specific dose of a therapeutic agent is being administered. Confirmation of appropriate activation of the implantable drug delivery device (e.g., the opening of a drug barrier layer) by visible observation is contemplated to provide both a quick and unequivocal indication of drug release. However, if direct observation of the therapeutic agent itself is not feasible, a surrogate marker is employed to indirectly monitor release or exposure of the therapeutic agent from a drug reservoir of the implantable medical drug delivery device. In some embodiments, the surrogate marker is conjugated to the therapeutic agent so that the surrogate marker-therapeutic agent can be directly monitored.

The present disclosure relates to the use of an implantable drug delivery device comprising one or more drug reservoirs containing a therapeutic agent to be released or exposed by a physician or other healthcare provider, as needed. In preferred embodiments, the drug reservoirs of the drug delivery device comprise a barrier layer that is impervious to the therapeutic agent(s) contained therein. If the drug delivery device is rod-like or cylindrical in shape, the barrier layer may extend circumferentially around the reservoir. In some embodiments, if necessary to the ensure the stability or viability of the therapeutic agent, the barrier layer is impervious to water, oxygen and/or other substances external to the barrier layer such as cells, enzymes, vitreous, etc., which may be deleterious to the therapeutic agent if it is exposed to these materials for a prolonged period of time prior to release. The barrier layer is breached by a laser or other means of selective destruction or alteration of the barrier. The ruptured barrier in turn, allows the contents of the reservoir(s) to elute into the tissue (e.g., interior of the eye) in a controlled, predetermined, manner.

I. Implantation and Irradiation

As mentioned above, a physician may rupture one or more reservoirs of an implanted drug delivery device to release a therapeutic agent contained therein by applying laser light to the reservoir's barrier layer, as illustrated in FIG. 1.

The drug delivery devices are configured for implantation (e.g., surgery or injection) within or adjacent to a variety of body locations, including in an ocular region of a subject. In the example depicted in FIG. 2, drug delivery device 100 is shown being injected into the ocular region of the subject by a needle 212. The needle may comprise a 20 gauge or smaller cannula. In these variations, the drug delivery devices are configured for placement within or adjacent to a sclera, a cornea, a choroid, a retina, a vitreous body, a pars plana, or a conjunctiva of an eye of a subject. Furthermore, in some examples, drug delivery devices are configured so that, when placed in an ocular region, they do not contact the retina or lens.

Referring back to FIG. 1, drug delivery device 100 is configured to fit within the vitreous 102 at the back of an eye 105. An external light source 110 (e.g., a laser available to retinal specialists) is used to irradiate a reservoir 130 in drug delivery device 100 to release a therapeutic agent 104 directly into the eye 105 so that it can reach a desired target in the retinal region 103. The radiation 112 emitted from the external light source 110 is not significantly absorbed by any portion of drug delivery device 100 except a barrier layer of a reservoir 130, thereby allowing selective release of the therapeutic agent 104 from the illuminated reservoir. In some cases, the radiation 112 is not significantly absorbed by tissues adjacent to drug delivery device 100, thereby reducing the probability of damage to the tissues.

The drug delivery device 100 shown in FIG. 1 has one breached (unsealed) reservoir 130, and four unbreached (sealed) reservoirs that sequester a therapeutic agent 104 from the vitreous 102 until which time a further dose is needed. It is understood that FIG. 1 shows one example and the number of reservoirs in other drug delivery devices can be greater or less than five. It should also be understood that the order of breaching the reservoirs with an external light source may be in any order. In other words, reservoirs can be breached in sequential order, but can also be breached in an nonsequential order.

Drug delivery device 100 is illustrated in FIG. 3. Drug delivery device 100 comprises multiple reservoirs 128, 129, 130, 131 and 132. In this particular example, the reservoirs 128, 129, 130, 131 and 132 are arranged in a linear array along the device body. The reservoirs 128, 129, 130, 131 and 132 may be separated by separation members 106, which may comprise membranes, valves, and/or walls, as discussed above. The drug delivery devices may have a configuration, geometry, and/or dimensions that are suitable for ocular implantation. A drug delivery device for use in the eye may be designed for implantation into the vitreous cavity, the retina, the sclera, the cornea, the conjunctiva, or any space or potential space within the orbit or eye itself. For example, if a device is to be implanted in the vitreous, the device may have dimensions such that the device will not reach the retinal tissue or the lens to reduce the probability of interference with vision and/or injury to those areas.

Figure 2:
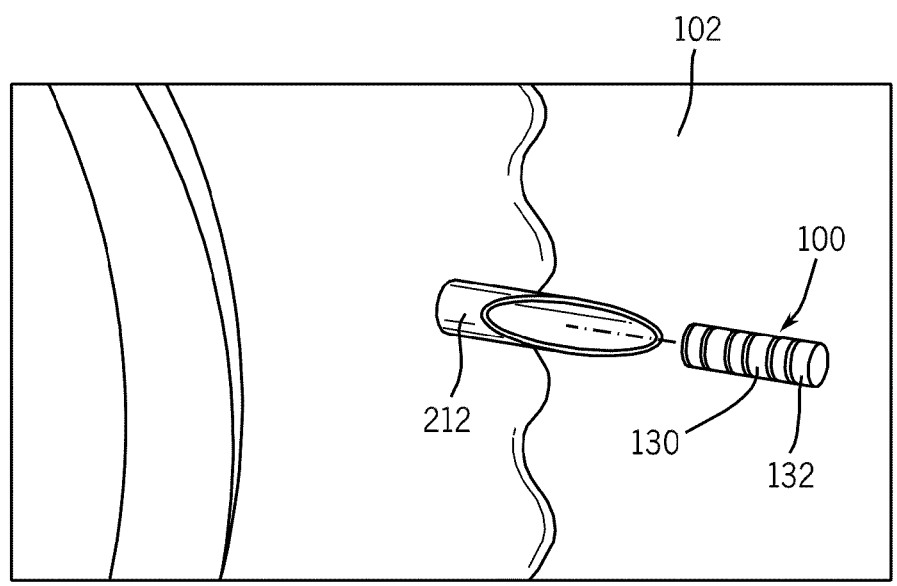
FIG. 2 illustrates the embodiment of the drug delivery device being implanted into the eye by a needle.

Further, the device 100 has an elongated delivery configuration, which may fit into a cannula needle (e.g., a 20 gauge, a 21 gauge, a 23 gauge, a 25 gauge, a 30 gauge or even smaller cannula), as illustrated in FIG. 2.

Drug delivery devices may be rigid in some examples. In other examples, the drug delivery devices may be at least partially flexible to assist the devices in conforming to a subject's anatomy, e.g., the vitreous cavity in an eye. For example, the drug delivery device may comprise a flexible body, or relatively rigid device body sections that may, for example, be interconnected with flexible members. Drug delivery devices may comprise a unitary body that comprises one or more reservoirs, or they may comprise multiple body sections that each may comprise one or more drug reservoirs. In these instances, the reservoirs may be arranged within multiple device body sections that may or may not be coupled together.

Within a device, the reservoirs themselves may have a variety of configurations. For example, the reservoirs may comprise open, hollow volumes within device bodies, or they may comprise one or more plugs, replacement reservoirs, or the like inserted into device bodies. The reservoirs may have the same or different sizes and/or shapes within the same device. For example, a device body may comprise multiple similar or equally-sized sections, where single ones of these sections may be used to form some reservoirs, and multiple ones of these sections may be joined together to form a reservoir that is larger than other reservoirs in the same device. Adjacent reservoirs may be separated from each other using any suitable type of separation member. For example, reservoirs may be separated by an impenetrable barrier (e.g., a solid wall), a penetrable barrier, or a valve (e.g., a one-way valve that allows the reservoir to be loaded, but prevents backwards flow out of the reservoir).

Although the figures show the devices having certain numbers of reservoirs and having certain shapes, dimensions, geometries, configurations, etc., any suitable number of reservoirs may be included in the devices, and the devices may have any suitable shape, dimensions, geometry, and configuration.

FIG. 3 illustrates drug delivery device 100 having a rod-like, or cylindrical shape and a round cross-section. However, other examples of drug delivery devices may comprise a bent, curved, helical, coiled, serpentine, zigzag-type, or other non-linear type of device body structure. Furthermore, other examples of drug delivery devices may have cylindrical, quadrilateral, ellipsoidal, polyhedral, or irregular cross-sections.

Some drug delivery devices are configured to free-float in the vitreous or other part of the orbit or eye upon implantation. However, other drug delivery devices may comprise a tether or other feature to allow repositioning, retrieval and/or securing the device while it is implanted in the body. Variations of drug devices may comprise an attachment configured to allow the device to be secured to the subject's anatomy. Such attachments may allow permanent or temporary securing of the drug device to the anatomy, e.g., attachments may be biodegradable to dissolve over time.

The drug delivery devices may be configured to deliver any suitable agent (i.e., drug) or combination of agents to a subject. In drug delivery devices comprising multiple reservoirs, two or more of the reservoirs may comprise the same agent, e.g., to deliver sequential doses of that agent. Reservoirs may be loaded with multiple agents that are selected to be at least part of a combination drug therapy, e.g., a concomitant drug therapy that comprises the simultaneous delivery of multiple agents and/or a sequential drug therapy that comprises the sequential delivery of multiple agents.

As illustrated in FIG. 3, for example, in some variations, a target region may comprise a band that extends circumferentially around at least part of a circumference of the device. This latter geometry may allow improved access to the target region from an externally directed triggering stimulus (e.g., a laser) even if the device rotates in vivo.

In some variations, lens 101 (FIG. 1) is used between light sources 110 and the eye to filter the light and/or direct it onto a barrier of a sealed reservoir. In other variations, the filtering/focusing lens 101 is placed directly on the eye. In some embodiments, the drug reservoirs 132 comprise sequential doses, which may be unit doses, of the same or a similar therapeutic agent to treat chronic conditions (e.g., age-related macular degeneration, diabetic retinopathy, etc.). In those circumstances, drug delivery devices 100 may be left in the eye for years, with the spacing between doses being on the order of weeks, months or longer.

Verification of Therapeutic Agent Release

Figure 4:
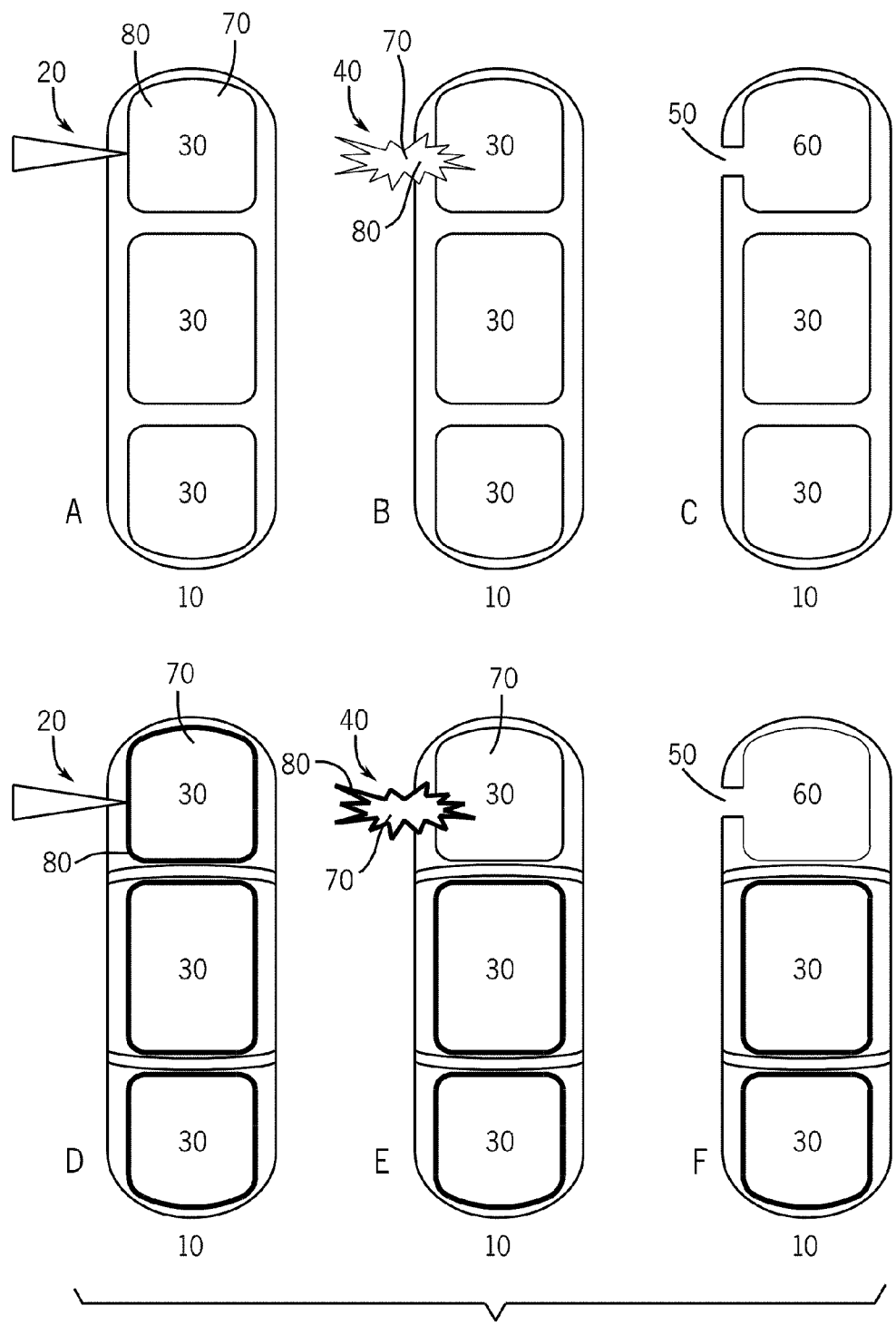
FIGS. 4A-C and 4D-F illustrate two embodiments of a drug delivery device.

FIGS. 4A-4F illustrate examples of visual indicators for verifying the release of therapeutic agents from the drug delivery device. In some embodiments, a visual indicator is a marker. Referring now to the upper portion of FIG. 4A, drug delivery device 10 is shown during laser activation 20. FIG. 4B shows the laser-induced rupture 40 of a reservoir 30, thereby releasing a marker 80 and a therapeutic agent 70 contained within the ruptured reservoir. FIG. 4C shows an opening in a barrier layer 50 of the drug delivery device 10, and a spent reservoir 60. The marker 80 is bioabsorbable, biodegradable, or otherwise temporary after release from the drug reservoir, in some preferred embodiments of the disclosure. The marker 80 may be chemically bound to the therapeutic agent 70, or it may exist in a simple mixture with the therapeutic agent 70.

Alternatively, referring to FIGS. 4D, 4E, and 4F, the marker 80 may be an independent layer coated on the outside of the therapeutic agent 70, an independent layer on the internal surface of the barrier, or contained in one or more defined locations inside the quantity of therapeutic agent 70. Referring now to FIG. 4D, drug delivery device 10 during laser activation 20 is illustrated. FIG. 4E shows the laser-induced rupture 40 of a reservoir 30. The laser-induced rupture 40 releases both therapeutic agent 70, as well as marker 80 from the outer envelope of marker. FIG. 4F shows an opening in a barrier layer 50 of the drug delivery device 10, and a spent reservoir 60.

In some embodiments, the marker 80 may also be contained in a dye pellet within the drug reservoir (not shown). In some embodiments, a low volume fraction of a marker 80 is included within or surrounds the drug reservoir 30.

Examples of markers 80 include but are not limited to dyes, stains, fluorophores, phosphors, and bioluminescent substances. In this way the physician or other health care provider receives immediate, visual feedback that a reservoir barrier has been activated (e.g., perforation, change in permeation, breeching, destruction, etc.) and that the therapeutic agent(s) 70 contained therein will consequently be released. Particularly suitable examples of markers 80 include, but are not limited to, fluorescein, rose Bengal, indocyanine green, rhodamine, other dyes safely used in the eye, or the flourophore. A fluorophore marker released from a drug delivery device is shown in FIG. 5 and described in further detail below in Example 1.

In some embodiments, the marker 80 is not visible to the naked eye so as avoid obscuring the patient's vision, but can be visualized upon external excitation. In a preferred variant of this embodiment, the marker 80 is UVA excitable, such that under ordinary illumination, and for a drug delivery device deployed in the eye, the patient does not experience any visual field changes unless an ultraviolet light source is used to illuminate the patient's eye. In other embodiments, the marker is not visible until it is released into the ocular tissue from a drug reservoir of the drug delivery device. For instance, in some embodiments, the marker 80 is designed to change color when the local pH, salinity, hydration, etc., changes. This may occur, for example, when the marker 80 elutes from the environment inside the reservoir 30 into ocular tissue such as the vitreous humor in the posterior chamber or the aqueous humor in the anterior chamber of the eye.

Figure 6:
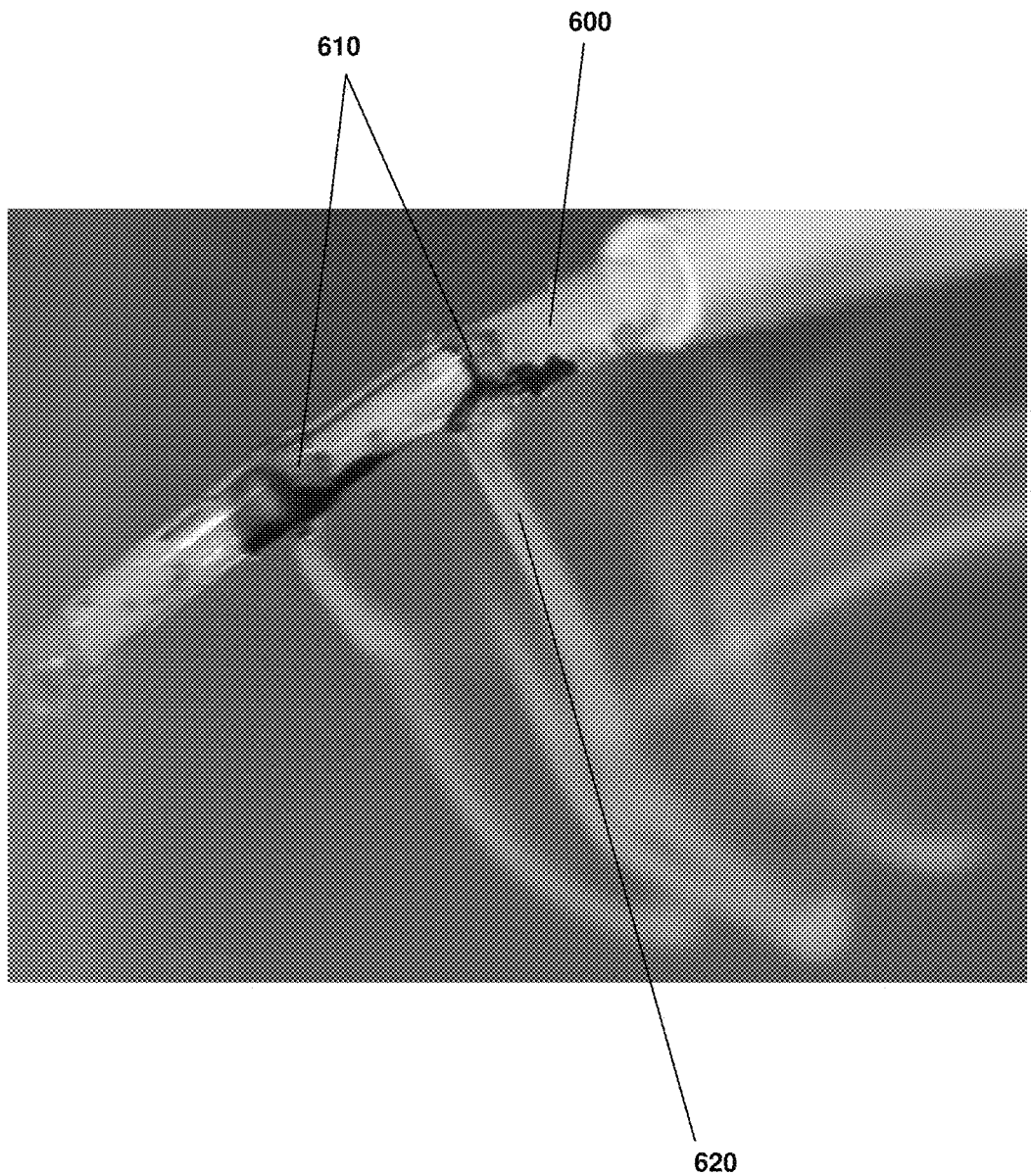
FIG. 6 illustrates an embodiment of a drug delivery device releasing a marker contained therein after a laser beam has perforated the barrier layer of a drug reservoir.

In some embodiments, one marker is employed, while in other embodiments, more than one marker is used (not shown). For example, an un-bound first marker can be used to indicate that a reservoir has been successfully activated, breached, opened, etc., by a laser or other means. A second, bound marker can be used to directly indicate the elution of the therapeutic agent. Another possibility is to encase the drug reservoir with a highly soluble outer dye layer possessing a thin protective coating. As such, when a laser is used to breach the drug reservoir barrier, the first soluble material to elute is the dye layer that encases the therapeutic agent. In some embodiments, the marker maybe covalently bound to the therapeutic agent. A release of two markers is shown in FIG. 6 and further described in Example 3 below.

In some embodiments, two or more markers are arranged spatially such that successive release of the markers indicates the stage of release of the therapeutic agents from the drug reservoirs. For example, one marker can be placed proximal to the activation site of the drug reservoir such that upon activation of the reservoir by irradiation of the activation site on the barrier wall, the underlying first marker is observable. A second marker can be placed distal to the activation site such that when the therapeutic agent located between the first and second markers has completely eluted, the second marker is observed to elute from the spent drug reservoir. Such arrangements require proper packaging, as well as engineering of the solubility of the contents of the drug reservoir.

Another consideration for the marker is time. Often the treating physician will want to know immediately whether the barrier has been activated, but will not have time to observe a slowly eluting visual indicator. An example of a slow visual indicator is a water-based dye mixed, bonded or otherwise coupled to a therapeutic agent of interest, which co-elutes into the vitreous of a posterior chamber of a patient's eye. Elution of a slow visual indicator may require a wait of ten minutes or longer before definitive confirmation of barrier activation on the basis of marker elution is provided. This wait may be too lengthy for a busy practitioner to accommodate. For this reason, in further embodiments described below, confirmation of barrier activation is made not on the basis of release of a marker, but on the basis of a visual change to the barrier (e.g., visibility of a drug pellet, deformation, air bubble, breech, alteration, perforation, etc.). In yet another embodiment, the barrier can be designed so that the barrier material changes color or shape when a sufficient amount of laser energy has been imparted on the barrier material to cause it to open or be perforated. These visual changes to the barrier as ways of confirmation of barrier activation can be made without the need of a marker. However, these ways of confirmation may also be used in conjunction with a marker.

In some embodiments, the implantable medical drug delivery devices are those described in U.S. 2009/0196903 of Kliman entitled "Drug Delivery Devices, Kits and Methods, Therefor," which is herein incorporated by reference. In some embodiments, the exterior appearance of the drug reservoirs of suitable implantable medical drug delivery devices are made distinct through the use of different colors, dyes, etc., in order to initially distinguish between reservoirs. The exterior of the drug delivery device can have numbers, figures, stripes, or other symbols drawn or etched into the barrier material over each reservoir, allowing the physician to quickly determine the contents of that reservoir (drug, dose, marker, etc). The physician or health care provider can also use such markings to determine which reservoirs have been opened in the past by comparing the markings with records from past office visits.

An example of a drug delivery device having markings on the exterior of the drug delivery device is illustrated in FIG. 5. Drug delivery device 500 includes multiple reservoirs with markings of numbers. For example, reservoir 502 is marked with "1", reservoir 504 is marked with "2", and reservoir 506 is marked with "3". The numbers may be etched into or drawn on the barrier layers of each reservoir. Furthermore, the markings may appear around the circumference of drug delivery device 500 such that the markings can be visualized by the physician regardless of the rotation of drug delivery device 500 in the eye. For example, the markings may be located around each barrier layer at every 60 or 90 degrees. In other examples, the markings may be one or more of symbols, letters, numbers, colored regions, or any combination thereof, for example.

Additional visual indicators may be employed to distinguish between reservoirs prior to activation, to determine when a particular reservoir has been activated, or to distinguish the contents released by activated reservoirs. For instance, a blister or melt artifact from heating a barrier layer of a drug reservoir may be used to determine whether a drug reservoir has been opened. A characteristic foamy appearance of a laser-heated polymer wall is reliably produced when a polymer barrier layer, such as a thin-walled layer of high density polyethylene, has been perforated. In these ways, there is a visual indication confirming the release of the therapeutic agent from a reservoir. A marker may or may not be used in conjunction with these visible structural changes to confirm release of the therapeutic agent from the reservoir.

Other embodiments satisfying the requirement for a rapid indication of activation of a drug reservoir barrier include the induction of a small gas bubble, which is visible at the laser activation site. This bubble may, for example, be forced out from inside a porous cake or matrix containing a therapeutic agent inside the drug reservoir. Alternatively, the bubble may be produced by thermal evaporation of water by heating the barrier with a laser. In further embodiments, the visual indicator is provided in the form of a direct observation of a laser-generated hole or feature. If a color contrast exists between the wall of the barrier and the payload inside a reservoir, a direct visualization of the contrast of the interior content against the barrier structure provides a suitable visual indication. Similarly, multiple therapeutic agent payloads may be colored, dyed, or otherwise made visually distinct from both the drug reservoir barrier and from each other. In some embodiments, the barrier is transparent or translucent. This permits the reservoir interior to be observed to indicate when a drug reservoir barrier has been activated, and to distinguish between different therapeutic agents that may variously populate multiple drug reservoirs of the implantable medical device. In further embodiments, the barrier is colored and the barrier breech or activation reveals a contrasting color of a tablet including the therapeutic agent through the barrier opening.

After an initial release of a therapeutic agent from the first drug reservoir of a drug delivery device containing multiple drug reservoirs, subsequent release events are initiated. During subsequent drug delivery device activations, the treating physician may be unable to observe the initial visual indicator (e.g., perforation of the barrier wall of the first drug reservoir of the drug delivery device because the drug delivery device has moved (e.g., rotated) or because the physician is observing the drug delivery device from a different angle. As such, in some embodiments a specific color present in the drug payload provides a further visual indicator to distinguish between a drug-filled (loaded) reservoir and an empty (unloaded) reservoir. In a particular embodiment, the drug delivery device tubing wall in thin sections is translucent or transparent, allowing an observer to visualize the color or pigmentation of the contents of in a particular reservoir. In some embodiments, full reservoirs are designed to show a particular color corresponding to a particular type of marker or therapeutic, while empty reservoirs are devoid of color. In another embodiment, the shape of the reservoir and/or barrier wall can indicate if the reservoir contains drug or is empty. For example, full reservoirs may have flat walls or walls that bulge outward, but once the drug has been released from the drug delivery device, the reservoir walls may look compressed or caved in, indicating no drug is in the reservoir.

It should be understood that the terms "drug," "therapeutic agent," and "formulation" are used interchangeably herein. Therapeutic agents may be selected from the classes of agents including anti-inflammatories (e.g., steroidal and non-steroidal), anti-infectives (e.g., antibiotics, antifungals, antiparasitics, antivirals, and antiseptics), anti-allergens, cholinergic antagonists and agonists, adrenergic antagonists and agonists, anti-glaucoma agents, neuroprotection agents, agents for cataract prevention or treatment, anti-oxidants, antihistamines, anti-platelet agents, anticoagulants, antithrombics, anti-scarring agents, anti-proliferatives, anti-tumor agents, complement inhibitors (e.g., anti-C5 agents, including anti-C5a and anti-C5b agents), decongestants, healing promoters, vitamins (e.g., vitamin B and derivatives thereof, vitamin A, depaxapenthenol, and retinoic acid), growth factors, agents to inhibit growth factors, gene therapy vectors, chemotherapy agents, protein kinase inhibitors, small interfering RNAs, and combinations thereof. Non-limiting, specific examples of drugs that may be used alone or as part of a combination drug therapy include LUCENTIS™ (ranibizumab), AVASTIN™ (bevacizumab), MACUGEN™ (pegaptanib), steroids, e.g., dexamethasone, triamcinolone, and fluocinolone, taxol-like drugs, vascular endothelial growth factor (VEGF) trap (aflibercept), anecortave acetate (Retaane), and limus family compounds. Non-limiting examples of members of the limus family of compounds include sirolimus (rapamycin), tacrolimus, everolimus, pimecrolimus, zotarolimus, temsirolimus, AP23841 (Ariad), and the like, as well as analogs and derivatives thereof.

Example 1

Visualization of a Laser-Activated Fluorophore Release

In a proof of concept demonstration, illustrated in FIG. 6, a drug delivery device 600 was fabricated as a tubular polymeric device. Drug reservoir 610 of the exemplary drug delivery device was filled with a composition comprising a dexamethasone salt and sodium fluorescein. The drug delivery device 600 was placed within an acceptor compartment of a Franz cell. A Franz cell is a specially designed apparatus that allows for the determination of the precise amount of bioactive compound that has penetrated through a membrane. The membrane is positioned between an upper donor chamber and a lower acceptor chamber. A laser was used to irradiate the drug delivery device with a wavelength at 532 nm through a membrane separating the donor and acceptor compartments of the Franz cell. The laser-induced rupture of the drug reservoir was verified by visually observing a fluorescent streams 620 emanating from the drug delivery device into the aqueous medium of the acceptor compartment.

Example 2

Visualization of a Laser-Activated Reservoir Breach

In a further proof of concept demonstration, a tubular polymeric drug delivery device (black polyolefin shrink tube) was fabricated. A drug reservoir of the exemplary drug delivery device was filled with a composition comprising a dexamethasone salt and sodium fluorescein. The drug delivery device was placed within the vitreous of an eye of an albino pig using an 18 gauge needle. A laser was used to irradiate the drug delivery device with a wavelength of 532 nm (750-1000 mw, 50 ms, 50 μm laser pulse) to rupture the barrier layer to elute the dexamethasone salt and sodium fluorescein mixture contained within the drug reservoir. A sample of the vitreous containing the activated drug delivery device was removed from the eye and placed in a cuvette for observation of the drug delivery device over time. The laser-induced rupture of the drug reservoir was verified by visually observing formation of a gas bubble at the site upon which the laser beam was focused.

Example 3

Visualization of a Laser-Activated Exposure of Two Therapeutic Agents

Figure 7:
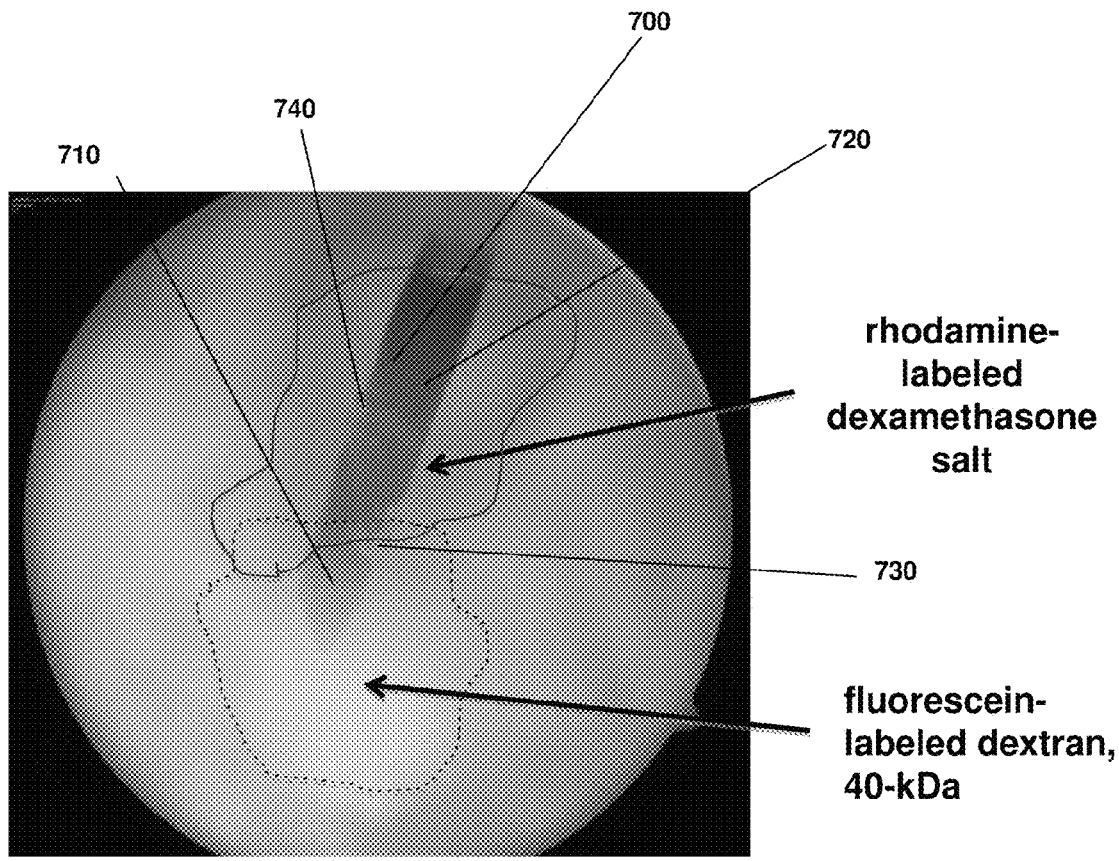
FIG. 7 illustrates an embodiment of a drug delivery device releasing one marker contained in one reservoir and a different second marker contained in a second reservoir after laser light has perforated the barrier layers of the two reservoirs.

In a further proof of concept demonstration, illustrated in FIG. 7, a tubular polymeric drug delivery device 700, made from black polyolefin shrink tube, containing two drug reservoirs separated by a divider was fabricated. A first drug reservoir 710 of the exemplary drug delivery device 700 is filled with a composition comprising a dexamethasone salt and a fluorescein salt. A second drug reservoir 720 of the exemplary drug delivery device 700 is filled with a composition comprising a dexamethasone salt and a rhodamine salt. The drug delivery device is placed within the vitreous of an eye of an albino pig using an 18 gauge needle. A laser is used to irradiate the drug delivery device with a wavelength of 532 nm (750-1000 mw, 50 ms, 50 μm laser pulse) to rupture the barrier layer of the first drug reservoir to elute the dexamethasone salt and fluorescein salt mixture contained within the first drug reservoir 710. A laser is then used to irradiate the drug delivery device with a wavelength of 532 nm (750-1000 mw, 50 ms, 50 μm laser pulse) to rupture the barrier layer of the second drug reservoir 720 to elute the dexamethasone salt and rhodamine salt mixture contained within the second drug reservoir. As described above, air bubble 730 associated with the opening of first drug reservoir 710 is illustrated in FIG. 7. Similarly, air bubble 740 associated with the opening of second drug reservoir 720 is also illustrated. Air bubbles 730 and 740 visually indicate to the physician or other health care provider that first drug reservoir 710 and second drug reservoir 720 have been successfully opened by the laser irradiation. A sample of the vitreous containing the activated drug delivery device is removed from the eye and placed in a cuvette for observation of the drug delivery device over time. The laser-induced rupture of the two drug reservoirs is verified by visually observing formation of an air bubble at the sites upon which the laser beam was focused. In addition, the laser-induced rupture of the two drug reservoirs is verified by visually observing a fluorescein (yellow) stream and a rhodamine (red) stream emanating from the breached reservoirs of the drug delivery device into the vitreous ex vivo.

This disclosure is illustrative and not limiting. Further modifications will be apparent to one skilled in the art in light of this disclosure and such modifications are intended to fall within the scope of the appended claims.

What is claimed is:

1. A method comprising:
   a. implanting a drug delivery device within or adjacent to an ocular region of a subject, wherein the drug delivery device comprises:
      i. a plurality of reservoirs, each loaded with a therapeutic agent and a marker; and
      ii. a plurality of barrier layers, each separating contents of one of the plurality of reservoirs from the ocular region;
   b. irradiating at least one of the plurality of barrier layers such that at least one of the plurality of barrier layers is breached, thereby triggering release of the marker from the reservoir of the device; and
   c. visibly observing release of the marker into the ocular region with visible light in order to verify exposure of the therapeutic agent to the ocular region.

2. The method of claim 1, wherein the therapeutic agent comprises one or more of the group consisting of anti-inflammatories, anti-infectives, anti-allergens, cholinergic agonists and antagonists, adrenergic agonists and antagonists, anti-glaucoma agents, agents for cataract prevention or treatment, neuroprotection agents, anti-oxidants, antihistamines, anti-platelet agents, anti-coagulants, anti-thrombic agents, anti-scarring agents, anti-proliferatives, anti-tumor agents, complement inhibitors, decongestants, vitamins, growth factors, anti-growth factor agents, gene therapy vectors, chemotherapy agents, protein kinase inhibitors, small interfering RNAs, limus family compounds, and combinations thereof.

3. The method of claim 2, wherein the anti growth factor agent is an anti-vascular endothelial growth factor (anti-VEGF) agent.

4. The method of claim 3, wherein the anti-VEGF agent is selected from the group consisting of aflibercept (VEGF trap), bevacizumab (AVASTIN), pegaptanib sodium (MACUGEN), and ranibizurnab (LUCENTIS).

5. The method of claim 1, further comprising:
   d. distinguishing between an unloaded reservoir and at least one loaded reservoir, wherein the unloaded reservoir is produced due to essentially complete release of the therapeutic agent and the marker, and wherein the at least one loaded reservoir still contains additional therapeutic agent and additional marker;
   e. irradiating at least one of the plurality of barrier layers such that the at least one loaded reservoir is breached, thereby triggering exposure of the additional therapeutic agent and the additional marker from the device; and
   f. visibly observing release of the additional marker from the loaded reservoir into the ocular region with visible light in order to verify exposure of the additional therapeutic agent to the ocular region.

6. The method of claim 5, further comprising repeating steps d-f until all of the plurality of reservoirs are unloaded reservoirs.

7. The method of claim 1, wherein release of the marker from the reservoir into the ocular region occurs prior to release of the therapeutic agent from the reservoir into the ocular region.

8. The method of claim 7, wherein visibly observing release of the marker from the reservoir into the ocular region occurs prior to release of the therapeutic agent from the reservoir into the ocular region.

9. The method of claim 1, wherein the marker is a fluorophore, and wherein the fluorophore is selected from the group consisting of fluorescein, rose Bengal, indocyanine green, and rhodamine.

10. The method of claim 1, wherein the irradiating comprises an application of energy from a laser, wherein the laser is selected from the group consisting of an argon ion laser, a Nd:YAG laser, a frequency-doubled Nd:YAG laser, a diode laser, a Nd:YLF laser, a krypton laser, a dye laser, and a helium-neon laser.

11. The method of claim 1, wherein the ocular region comprises a sclera, a cornea, a choroid, a retina, a vitreous body, a pars plana, or a conjunctiva.

12. The method of claim 1, wherein the implanting comprises intravitreal injection or insertion of the device.

13. The method of claim 1, wherein the marker is unbound from the therapeutic agent.

14. The method of claim 1, wherein the marker comprises a coating on an internal surface of the reservoir.

15. The method of claim 1, wherein the drug delivery device further comprises a second marker arranged spatially in the reservoir with the therapeutic agent and the marker, the method further comprising visibly observing release of the second marker into the ocular region with visible light in order to verify complete release of the therapeutic agent into the ocular region.

16. A method comprising:
   a. implanting a drug delivery device within or adjacent to an ocular region of a subject, wherein the drug delivery device comprises:
      i. a plurality of reservoirs, each loaded with a therapeutic agent; and
      ii. a plurality of barrier layers, each separating contents of one of the plurality of reservoirs from the ocular region;

b. irradiating at least one of the plurality of barrier layers such that at least one of the plurality of reservoirs becomes a breached reservoir that generates or exposes a visual indicator; and
c. visibly observing the visual indicator with visible light in order to verify exposure of the therapeutic agent to the ocular region.

17. The method of claim 16, further comprising:
d. distinguishing between an unloaded reservoir and at least one loaded reservoir, wherein the unloaded reservoir is produced due to essentially complete release of the therapeutic agent, and wherein the at least one loaded reservoir still contains the therapeutic agent;
e. irradiating at least one of the plurality of barrier layers such that the at least one loaded reservoir becomes a breached reservoir that generates or exposes the visual indicator; and
f. visibly observing the visual indicator with visible light in order to verify further exposure of the therapeutic agent to the ocular region.

18. The method of claim 17, further comprising repeating steps d-f until all of the plurality of reservoirs are unloaded reservoirs.

19. The method of claim 16, wherein the visual indicator comprises an air bubble and the visually detecting with visible light is accomplished by use of an ophthalmic slit-lamp microscope.

20. The method of claim 16, wherein the visual indicator comprises a hole in the barrier layer and the visually detecting with visible light is accomplished by use of an ophthalmic slit-lamp microscope.

21. The method of claim 16, wherein the visual indicator comprises a predetermined color of the barrier layer, and wherein the predetermined color indicates a ruptured barrier layer.

22. The method of claim 16, wherein the visual indicator is a shape of the barrier layer.

* * * * *